United States Patent
Audigier et al.

(10) Patent No.: US 10,748,438 B2
(45) Date of Patent: Aug. 18, 2020

(54) SYSTEM AND METHOD FOR INTERACTIVE PATIENT SPECIFIC SIMULATION OF RADIOFREQUENCY ABLATION THERAPY

(71) Applicant: Siemens Healthcare GmbH, Erlangen (DE)

(72) Inventors: Chloe Audigier, Valbonnes (FR); Tommaso Mansi, Plainsboro, NJ (US); Viorel Mihalef, North Brunswick, NJ (US); Ali Kamen, Skillman, NJ (US); Dorin Comaniciu, Princeton Junction, NJ (US); Puneet Sharma, Monmouth Junction, NJ (US); Saikiran Rapaka, Ewing, NJ (US)

(73) Assignee: Siemens Healthcare GmbH, Erlangen (DE)

( * ) Notice: Subject to any disclaimer, the term of this patent is extended or adjusted under 35 U.S.C. 154(b) by 927 days.

(21) Appl. No.: 14/769,844

(22) PCT Filed: Feb. 24, 2014

(86) PCT No.: PCT/US2014/017886
§ 371 (c)(1),
(2) Date: Aug. 24, 2015

(87) PCT Pub. No.: WO2014/133924
PCT Pub. Date: Sep. 4, 2014

(65) Prior Publication Data
US 2016/0022369 A1 Jan. 28, 2016

Related U.S. Application Data

(60) Provisional application No. 61/769,409, filed on Feb. 26, 2013.

(51) Int. Cl.
| | |
|---|---|
| *G01N 33/48* | (2006.01) |
| *G09B 5/02* | (2006.01) |
| *A61B 34/10* | (2016.01) |
| *A61B 6/00* | (2006.01) |
| *A61B 6/03* | (2006.01) |
| *G16H 50/50* | (2018.01) |
| *G09B 23/30* | (2006.01) |
| *A61B 18/00* | (2006.01) |

(52) U.S. Cl.
CPC .............. *G09B 5/02* (2013.01); *A61B 6/032* (2013.01); *A61B 6/50* (2013.01); *A61B 6/5217* (2013.01); *A61B 34/10* (2016.02); *G09B 23/30* (2013.01); *G09B 23/303* (2013.01); *G16H 50/50* (2018.01); *A61B 2018/00404* (2013.01); *A61B 2018/00529* (2013.01); *A61B 2034/104* (2016.02); *A61B 2034/105* (2016.02); *A61B 2034/107* (2016.02)

(58) Field of Classification Search
None
See application file for complete search history.

(56) References Cited

U.S. PATENT DOCUMENTS

| 8,267,927 B2 | 9/2012 | Dalal et al. |
|---|---|---|
| 8,295,913 B2 | 10/2012 | Haras |
| 8,663,083 B2 | 3/2014 | Georgi et al. |
| 8,682,626 B2 | 3/2014 | Ionasec et al. |
| 9,277,970 B2 | 3/2016 | Mansi et al. |
| 9,846,765 B2 | 12/2017 | Audigier et al. |
| 2008/0300588 A1 | 12/2008 | Groth et al. |
| 2009/0124896 A1 | 5/2009 | Haras |
| 2009/0142740 A1 | 6/2009 | Liang et al. |
| 2009/0221999 A1 | 9/2009 | Shahidi |
| 2010/0081857 A1 | 4/2010 | Georgi et al. |
| 2010/0168725 A1 | 7/2010 | Babkin et al. |
| 2011/0015628 A1 | 1/2011 | Dalal et al. |
| 2011/0196385 A1 | 8/2011 | Altrogge |

(Continued)

FOREIGN PATENT DOCUMENTS

| CN | 101563041 A | 4/2010 |
|---|---|---|
| CN | 102346811 A | 2/2012 |

OTHER PUBLICATIONS

Office Action dated Sep. 21, 2017 in corresponding Chinese application No. 201480010589.1.
Peng, T. et al.: "A two-equation coupled system for determination of liver tissue temperature during thermal ablation"; International Journal of Heat and Mass Transfers (2011); vol. 54; pp. 2100-2109.
PCT International Search Report dated May 9, 2014 corresponding to PCT International Application No. PCT/US2014/017886 filed Feb. 24, 2014 (12 pages).
Payne et al; "Image-Based Multi-Scale Modelling and Validation of Radio-Frequency Ablation in Liver Tumours"; philosophical transactions of the royal society A: MAthematical, Physical and engineering sciences; vol. 369; pp. 4233-4254; ISSN: 1095-9572; DOI: 10.1098/rsta.2011.0240; XP0055115338; 2011.

(Continued)

*Primary Examiner* — Anna Skibinsky (57) ABSTRACT

A method and system for interactive patient-specific simulation of liver tumor ablation is disclosed. A patient-specific anatomical model of the liver and circulatory system of the liver is estimated from 3D medical image data of a patient. A computational domain is generated from the patient-specific anatomical model of the liver. Blood flow in the liver and the circulatory system of the liver is simulated based on the patient-specific anatomical model. Heat diffusion due to ablation is simulated based on a virtual ablation probe position and the simulated blood flow in the liver and the circulatory system of the liver by solving a bio-heat equation for each node on the level-set representation using a Lattice-Boltzmann method (LBM) implementation. Cellular necrosis in the liver is computed based on the simulated heat diffusion. Visualizations of a computed necrosis region and temperature maps of the liver are generated. A user input is interactively received to modify the position of the virtual ablation probe, the heat diffusion and cellular necrosis is re-simulated based on the user input, and the visualizations of the computed necrosis region and the temperature maps are updated.

57 Claims, 5 Drawing Sheets

(56) References Cited

U.S. PATENT DOCUMENTS

| | | |
|---|---|---|
| 2011/0251607 A1 | 10/2011 | Kruecker et al. |
| 2013/0035921 A1 | 2/2013 | Rodriguez-Ponce et al. |
| 2013/0158577 A1 | 6/2013 | Mahon et al. |
| 2014/0022250 A1 | 1/2014 | Mansi et al. |

OTHER PUBLICATIONS

Craciunescu et al; "Discretizing large traceable vessels and using DE-MRI perfusion maps yields numerical temperature contours that match the MR noninvasive measurementsa"; Medical Physics, AIP; vol. 28; No. 11; pp. 2289-2296; ISSN: 0094-2405; DOI: 10.1118/1.1408619; XP012011333; 2001.

Van Den Berg et al; "Towards patient specific thermal modelling of the prostate"; Physics in Medicina and biology, Institute of Physics Publishing; vol. 51; No. 4; pp. 809-825; ISSN: 0031-9155; DOI: 10.1088/0031-9155/51/4/004; XP020096137; 2006.

Jayne et al., "Image-based Multi-Scale Modelling and Validation of Radio-Frequently Ablation in Liver Tumours", Philosophical Transactions of the Royal Society, 2011, vol. 369, pp. 4233-4254.

El-Serag et al., "The Continuing Increase in the Incidence of Hepatocellular Carcinoma in the United States: An Update," Ann Intern Me, 2003, vol. 139, pp. 817-823.

Chen et al., "Mathematical Modeling of Thermal Ablation inTissue Surrounding a Large Vessel", Journal of Biomechanical Engineering, 2009, vol. 131, pp. 011001-1 thru to 011001-5.

Jiang et al., "Formulation of 3D Finite Elements for Hepatic Radiofrequency Ablation", Int. J. Modelling, Identification and Control, 2010, vol. 9, No. 3, pp. 225-235.

Kröger et al., "Fast Estimation of the Vascular Cooling in RFA Based on Numerical Simulation", Open Biomed Eng J, 2010, vol. 4, pp. 16-26.

O'Neill et al., "A Three-State Mathematical Model of Hyperthermic Cell Death", Annals of Biomedical Engineering, 2011, vol. 39, pp. 570-579.

Rapaka et al., "LBM-EP: Lattice-Boltzmann Method for Fast Cardiac Electrophysiology Simulation from 3D Images", Medical Image Computing and Computer Assisted Intervention, 2012, vol. 7511, Springer Berlin Heidelberg, 2012, pp. 33-40.

Wissler, "Pennes' 1948 Paper Revisited: Analysis of Tissue and Arterial Blood Temperatures in the Resting Human Forearm," J Appl Physiol, 1998, vol. 85, No. 1, pp. 34-41.

Klinger, "Heat Transfer in Perfused Biological Tissue-I: General Theory", Bulletin of Mathematical Biology, 1974, vol. 36, pp. 403-415.

Grady, "Random Walks for Image Segmentation", IEEE Transactions on Pattern Analysis and Machine Intelligence, 2006, vol. 28, No. 11, 1-17 pgs.

Nakayama et al., "A General Bioheat Transfer Model Based on the Theory of Porous Media," International Journal of Heat and Mass Transfer, 2008, vol. 51, pp. 3190-3199.

Ralovich et al., "Hemodynamic Assessment of Pre- and Post-operative Aortic Coarctation from MRI," MICCAI 2012, Part II, LNCS 7511, pp. 486-493.

Chen et al., "Optimizing Electrode Placement Using Finite-Element Models in Radiofrequency Ablation Treatment Planning", IEEE Transactions on Biomedical Engineering, 2009, vol. 56, No. 2, pp. 237-245.

Schramm, "Contribution of Direct Heating, Thermal Conduction and Perfusion During Radiofrequency and Microwave Ablation," The Open Biomedical Engineering Journal, 2007, vol. 1, pp. 47-52.

Payne et al., "Image-based Multi-Scale Modelling and Validation of Radio-Frequently Ablation in Liver Tumours", Philosophical Transactions of the Royal Society, 2011, vol. 369, pp. 4233-4254.

Schenk et al., "Direct Measurement of Hepatic Blood Flow in Surgical Patients: With Related Observations on Hepatic Flow Dynamics in Experimental Animals", Annals of Surgery, 1962, pp. 463-469.

Pennes, "Analysis of Tissue and Arterial Blood Temperatures in the Resting Human Forearm", Journal of Applied Physiology, 1948, vol. 1, No. 2, pp. 93-122.

Payne, S. et al., "Image-based multiscale modelling and validation of radio-frequency ablation in liver tumours." Philosophical Transactions of the Royal Society A, Mathematical Physical and Engineering Sciences, published Oct. 3, 2011, pp. 4233-4254, Royal Society Publishing, Retrieved from the Internet at URL: http://rsta.royalsocietypublishing.org.†

Kerbl B. et al. (2012) Intervention Planning of Hepatocellular Carcinoma Radio-Frequency Ablations. In: Drechsler K. et al. (eds) Clinical Image-Based Procedures. From Planning to Intervention. CLIP 2012. Lecture Notes in Computer Science, vol. 7761. Springer, Berlin, Heidelberg. Retrieved from URL: https://link.springer.com/chapter/10.1007/978-3-642-38079-2_2.†

† cited by third party

Algorithm 1 Computational model of RFA

402 → 1: Estimate patient-specific model of liver anatomy
404 → 2: Compute 3D blood flow $\varphi_j$ and inlet pressures $p_j$ in hepatic vein
406 → 3: Compute portal vein upstream pressure $p^+$ by fitting Darcy's model to hepatic vein downstream pressures $p_j$ and flow $\varphi_j$
408 → 4: Compute 3D blood flow in portal vein
      5: while $t < t_{end}$ do
      6:    $t \leftarrow t + \Delta t$
410 → 7:    Update temperature $T$ using Pennes model in the large vessels, Wulff-Klinger model elsewhere
412 → 8:    Update cell-state

SYSTEM AND METHOD FOR INTERACTIVE PATIENT SPECIFIC SIMULATION OF RADIOFREQUENCY ABLATION THERAPY

This application claims the benefit of U.S. Provisional Application No. 61/769,409, filed Feb. 26, 2013, the disclosure of which is herein incorporated by reference.

BACKGROUND OF THE INVENTION

The present invention relates to ablation therapy planning, and more particularly to fast patient-specific simulation of tumor ablation using medical imaging data.

In spite of recent advances in cancer therapy, treatment of primary and metastatic tumors of the abdomen, including the liver, remains a significant challenge. Hepatocellular carcinoma (HCC) for example is one of the most common malignancies encountered throughout the world (more than 1 million cases per year), with increasing frequency in western countries due to the changing prevalence of hepatitis C. For both primary liver cancer and hepatic metastases, liver resection (partial hepatectomy) is the current preferred option in patients having confined disease. In selected cases of early HCC, total hepatectomy with liver transplantation may also be considered. Unfortunately, less than 25% of patients with primary or secondary liver cancer are candidates for resection or transplantation, primarily due to tumor type, location, or underlying liver disease. Consequently, increasing interest has been focused on ablative approaches for the treatment of unresectable liver tumors. Rather than extirpation, this technique uses complete local in situ tumor destruction. A variety of methods have been employed to locally ablate tissue. Radiofrequency ablation (RFA) is the most commonly used, but other techniques are also used, including ethanol injection, cryo-therapy, irreversible electroporation, and microwave ablation.

The RFA procedure is performed by placing a probe within the target area, the tumor. Electrodes at the tip of the probe create heat, which is conducted into the surrounding tissue, causing coagulative necrosis at temperatures between 50° C. and 100° C. In addition to increasing the number of patients eligible for curative therapy of liver cancer in unresectable patients, local tissue ablation has a significant advantage as it may be performed using a minimally invasive approach, including percutaneously and laparoscopically.

To place the probe at the target location, the physician relies on intra-operative imaging techniques, such as ultrasound. However, the success of the procedure depends on the optimal placement of the probe and heat delivery with respect to the circulation system and tissue properties of the liver and tumors. Different placements may have different results. The success of ablation is further challenged by the hepatic blood vessels that dissipate heat, thus potentially reducing RFA efficiency.

BRIEF SUMMARY OF THE INVENTION

The present invention provides a method and system for interactive patient-specific simulation of tumor ablation. Embodiments of the present invention focus on liver tumors and model the effects of ablation including heat diffusion, cellular necrosis, and blood flow through the vessels and liver. Starting from a preoperative medical image of a patient, such as a computed tomography (CT) or magnetic resonance imaging (MRI) image, the patient-specific geometry of the liver and venous system are automatically estimated. The vessel structure for the patient is accounted for as a heat sink in the model of biological heat transfer. Embodiments of the present invention utilize the Lattice Boltzmann method (LBM), which offers high parallel scalability, second order accuracy in space, and simplicity of implementation on a uniform Cartesian grid, to solve the biological heat transfer model. The use of the LBM allows for efficient interactive model computation. The biological heat transfer model is coupled to a computational fluid dynamics (CFD) solver to accurately take into account the effect of blood circulation on the dissipated heat. A cellular necrosis model is employed to simulate cell death due to over-heating and a computed necrosis area can be visualized along with the calculated temperature map over time.

In one embodiment of the present invention, a patient-specific anatomical model of the liver and venous system of the liver is estimated from medical image data of a patient. A computational domain is generated from the patient-specific anatomical model of the liver. Blood flow in the liver and the circulatory system of the liver is simulated based on the patient-specific anatomical model. Heat diffusion due to ablation based on a virtual ablation probe position and the simulated blood flow in the liver and the circulatory system of the liver is simulated by solving a bio-heat equation at each of a plurality of nodes of the computational domain. Cellular necrosis in the liver is computed based on the simulated heat diffusion and updating tissue parameters based on a computed cellular state.

These and other advantages of the invention will be apparent to those of ordinary skill in the art by reference to the following detailed description and the accompanying drawings.

DETAILED DESCRIPTION

The present invention relates to patient-specific modeling and simulation of tumor ablation using medical imaging data. Embodiments of the present invention are described herein to give a visual understanding of the methods for patient-specific modeling and simulation using medical imaging data, exemplified on the case of liver tumor. A digital image is often composed of digital representations of one or more objects (or shapes). The digital representation of an object is often described herein in terms of identifying and manipulating the objects. Such manipulations are virtual manipulations accomplished in the memory or other circuitry/hardware of a computer system. Accordingly, is to be understood that embodiments of the present invention may be performed within a computer system using data stored within the computer system.

Embodiments of the present invention utilize a computational framework for interactive, patient-specific planning of radio-frequency ablation. Starting from a preoperative 3D medical image, such as a computed tomography (CT) image, Magnetic Resonance Images (MRI), or ultrasound images, the geometry of the liver and the circulatory system is automatically estimated using an efficient algorithm. A bioheat equation is then solved on an isotropic Cartesian grid using the Lattice Boltzmann method (LBM) to obtain a temperature profile throughout the liver that varies over time. Embodiments of the present invention combine two different bio-heat models to cope with heat transfer due to different size blood vessels: the Pennes model close to larger vessels and the Wulff-Klinger model elsewhere to consider the effect of smaller vessels on heat diffusion. The bio-heat equation is coupled to a computational fluid dynamics (CFD) solver to accurately take into account the effect of blood circulation on the dissipated heat, while the blood flow in the porous liver tissue is calculated according to Darcy's law. Embodiments of the present invention compute the LBM and CFD on a Cartesian grid while the porous solver is executed on a tetrahedral mesh for increased accuracy. Tissue parameters are updated at every time step of the computation according to a cellular necrosis model to compute cell death due to over-heating.

Embodiments of the present invention provide a method for fast patient-specific simulation of liver tumor ablation that can be utilized with near real time interaction in a clinical setting. The LBM implementation for solving the bio-heat equation provides high parallel scalability, and therefore can be implemented on a massively parallel architecture, such as a graphics processing unit (GPU). Using such a parallel implementation, liver tumor ablation simulations can be performed efficiently in response to user interactions, which allows a user to interactively plan liver tumor ablation therapy using the simulations in a clinical setting.

Figure 1:
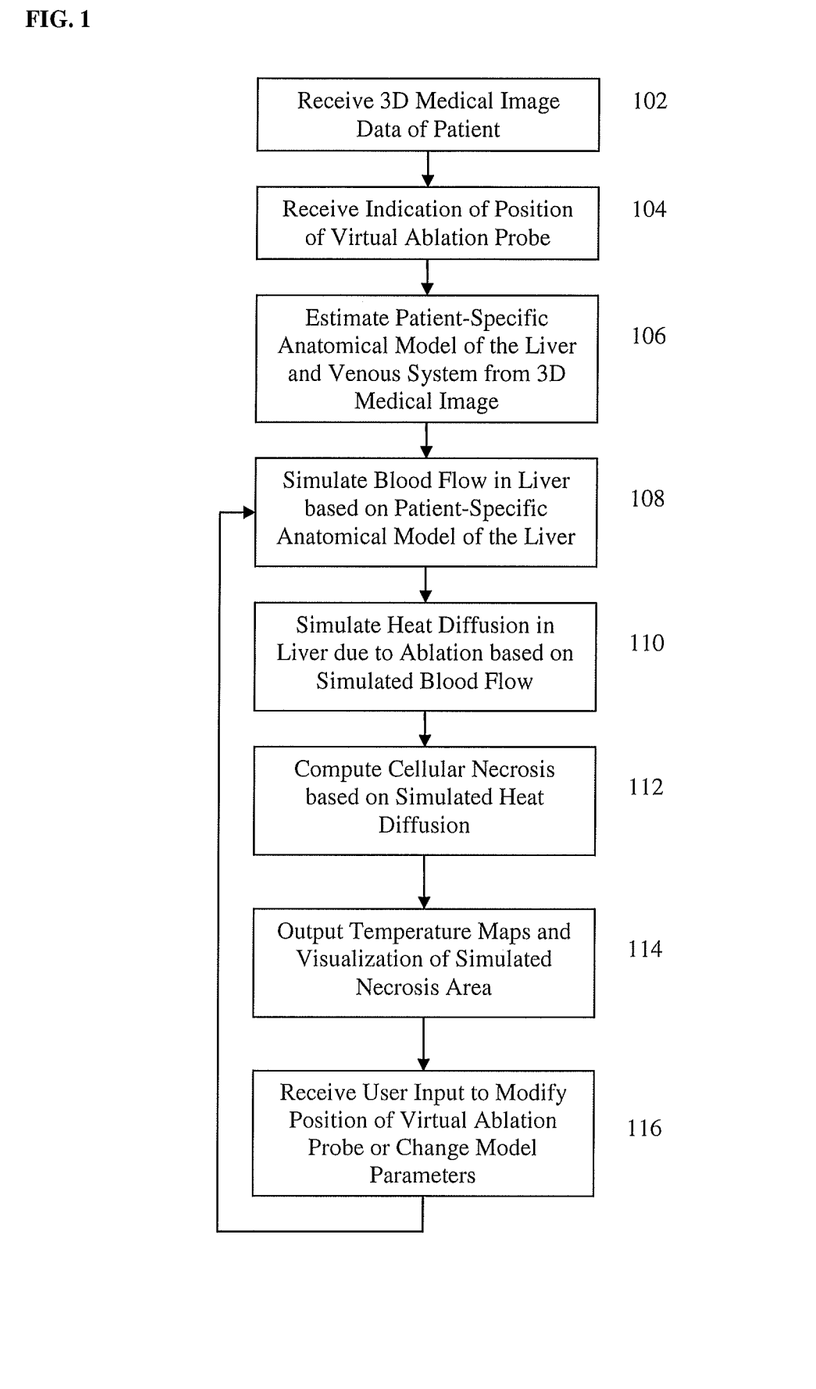
FIG. 1 illustrates a method for patient-specific simulation of liver tumor ablation according to an embodiment of the present invention.

FIG. 1 illustrates a method for patient-specific simulation of liver tumor ablation according to an embodiment of the present invention. The method of FIG. 1 transforms medical image data representing a patient's liver anatomy to provide patient-specific simulation of liver tumor ablation. At step 102, pre-operative 3D medical image data of at least of liver region of a patient is received. The pre-operative 3D image data can be acquired using any type of medical imaging modality, such as computed tomography (CT), three-dimensional rotational angiography, magnetic resonance imaging (MRI), ultrasound (US), positron emission tomography (PET), etc., provided that the liver is entirely visible in the medical image data. The medical image data can be received directly from an image acquisition device, such as a CT scanner, a C-arm image-acquisition device, an MRI scanner, or an US scanner, or the pre-operative cardiac image data can be received by loading previously stored cardiac image data of the patient. In a possible embodiment, a computed tomography, fluoroscopy, x-ray, or CT angiography system may be used to acquire the medical image data. The patient may receive a contrast agent that is generally opaque to x-rays. The contrast agent collects or is in the circulatory system, so vessels contrast with tissue. Any scanning sequence or approach may be used, such as CT angiography modes or rotational angiography to generate the pre-operative 3D medical image data.

At step 104, an indication of a position of a virtual ablation probe is received. In one embodiment, a user indication of a placement position of the ablation probe is received. The ablation is to occur near or in a lesion (e.g., tumor) or other region of tissue. Given anatomy, type of ablation, type of ablation device, or other limitations, the placement in the tissue may be limited. The user may indicate a possible placement of the ablation probe by selecting a location or locations in the pre-operative medical image data. For example, a location in a displayed multi-planar reconstruction of the patient can be selected by a user using an input device, such as a mouse, touch screen, etc. Although in FIG. 1, receiving an indication of the position of the virtual ablation probe (step 104) is shown as before the estimation of the patient-specific anatomical model from the medical image (step 106), it is to be understood that these steps can occur in either order or concurrently.

In a possible implementation, multiple positions of the ablation probe may be provided. For example, the user may indicate a sequence of placements for simulating sequential ablation operations or applications. In this case, the sequence is simulated by repeating steps 108-114 of FIG. 1 for each sequential probe position using the results from the previous run. Using the modeling of cellular necrosis in step 112, the changed tissue properties for various locations may be considered during the subsequent runs. Sequential placement may be used for larger tumors, where the single probe placement does not provide sufficient coverage of the thermal dose to the tumor. In another possible implementation, the user may indicate multiple placements for simulating ablation using multiple devices at a same time. The aggregated thermal dose is computed based on a single simulation run.

In an alternative embodiment, the user does not indicate placement. Instead, the position is selected automatically based on the image data, such as by identifying a center of the tumor. Various possible placements may be automatically identified and tested with separate simulations. In this case, the patient-specific anatomical model estimation (step 106) may be performed and then the position of the virtual ablation probe determined automatically based on the segmented tumor in the patient specific anatomical model. The position of the probe can also be automatically determined by maximizing the extent of necrosis. A map of potential probe locations can be automatically generated in this way and displayed to the user.

In addition to the position of the virtual ablation probe, the user may also input a spatial extent of the ablation probe, the type of ablation, duration, a desired dose, an indication of the spatial extent of the tumor, an indication of a location in the tumor, an amount of power for ablation, a type of ablation device, a sequence of power, and/or other characteristic of the ablation or tissue. Various inputs may be automated. Instead of user input, a processor provides the information.

At step 106, a patient-specific anatomical model of the liver and the circulatory system in the liver is estimated from the 3D medical image data. The patient-specific anatomical model is a detailed anatomical model of the patient's liver parenchyma, tumors, hepatic veins, vena cave, and portal vein. If visible, the hepatic artery can also be segmented. The 3D surface of the liver may be segmented automatically from the 3D medical image data. In one embodiment, the patient-specific anatomical model is semi-automatically estimated from the CT data using a graph theory approach, such as random walker segmentation. For each structure (parenchyma, tumors, hepatic veins, vena cava, portal vein, and hepatic artery), the user defines seeds inside and outside the area of interest. Then, the random-walker algorithm automatically estimates the boundary of the structure. The process may be refined by the user, interactively, if necessary. From the segmentation, a level set representation of the liver, minus the tumor and vessels, is calculated. Next, the resulting segmentations are merged into a multi-label mask image, which is then used to generate a tetrahedral multi-domain mesh.

Figure 2:
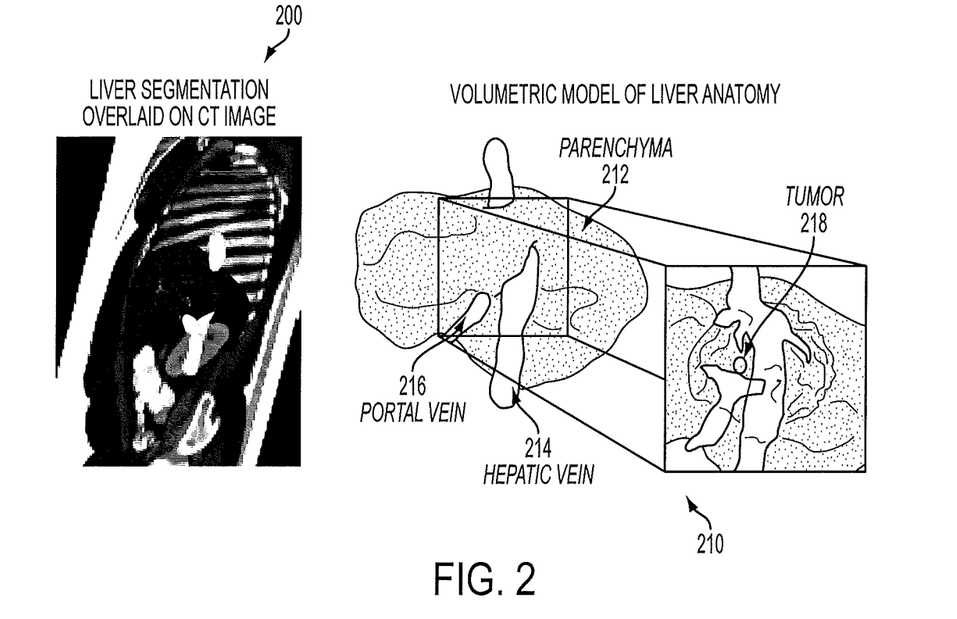
FIG. 2 illustrates exemplary results for estimating a patient-specific anatomical model of the liver.

FIG. 2 illustrates exemplary results for estimating a patient-specific anatomical model of the liver. As shown in FIG. 2, image 200 shows the liver segmentation 102 overlaid on a CT image. Image 210 shows the tetrahedral volume mesh generated from the liver segmentation, including the parenchyma 212, hepatic vein 214, portal vein 216, and a segmented tumor 218.

Returning to FIG. 1, at step 108, blood flow in the liver is simulated based on the patient-specific anatomical model of the liver and venous system. The blood flow through the venous system of the liver acts as a heat sink in diffusing the heat applying by the ablation probe. The blood flow in the patient-specific anatomic model is simulated in order to provide a personalized modeling of the heat sink due to the blood flow. Locations of the vessels in the tissue region, the size of the vessels, and/or other vessel characteristics are used to model the heat sink characteristics in the region of interest. The characteristics may be extracted from the segmented vessel information in the patient-specific anatomical model of the liver.

Figure 3:
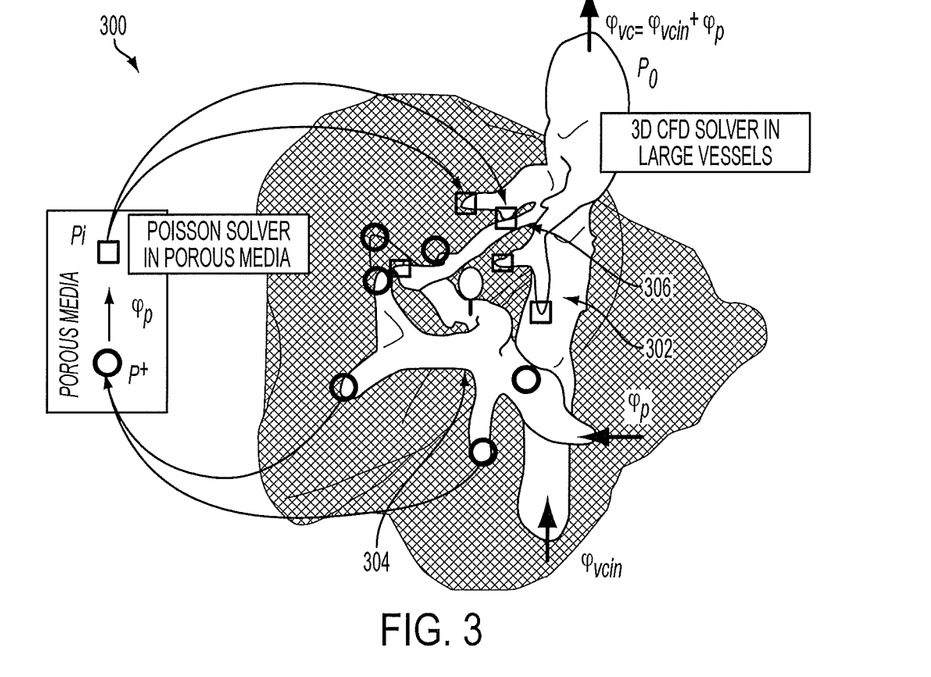
FIG. 3 illustrates an exemplary CFD model of the hepatic venous circulatory system.

The liver is treated as a porous media, so solving Darcy's law provides a velocity field throughout the organ that is used in the advection part of the heat transfer model. The blood velocity v inside the parenchyma is calculated according to Darcy's law: $v = -\kappa/(\mu \varepsilon^{2/3}) \nabla p$, where p is the pressure within the parenchyma and $\mu$ is the dynamic viscosity of the blood flow. This amounts to solving the Laplace equation $\nabla \cdot (-\kappa/(\mu \varepsilon^{2/3}) \nabla p) = 0$. At the border of the liver, Neumann boundary conditions are employed as no or little flow leaks outside the liver, whereas at the tip of portal and hepatic veins, Dirichlet boundary conditions are applied. Since the pressures cannot be estimated in-vivo, a computational fluid dynamics (CFD) model of the hepatic venous circulation system is used to estimate the pressures. FIG. 3 illustrates an exemplary CFD model of the hepatic venous circulatory system 300. As shown in FIG. 3, the hepatic venous circulatory system includes the vena cava 302, the portal vein 304, and hepatic veins 306. In FIG. 3, arrows denote blood flow, circles denote portal vein tips, and squares denote hepatic vein tips. Let $\varphi_{vc_{in}}$ the vena cava inflow, $\varphi_p$ the portal vein inflow, and $\varphi_{vc}$ be the vena cava outflow, which in virtue of conservation of mass is equal to $\varphi_{vc} = \varphi_{vc_{in}} + \varphi_p$, and $\varphi_i$ he flow through the inlets of the hepatic veins. The hepatic artery is ignored in this embodiment, but could be included without modifications to the framework described herein. A small pressure is assumed to exist at the outlet of the vena cava (e.g., $p_0 = 3$ mmHg), in the range of physiological values of healthy patients.

The blood flow and pressure distribution are computed within the vena cava (302 in FIG. 3) using three-dimensional computational fluid dynamics (e.g., using unsteady incompressible Navier-Stokes equations with viscous terms). The blood is modeled as a Newtonian fluid with pre-specified density $\rho_b$ and viscosity $\mu$ (see Table 1). The parameters may be different from one patient to another. A plug profile velocity field is applied at the inlets (squares in FIG. 3), computed from the outflow $\varphi_p$ and the cross-sectional area of each inlet. From the CFD computation, the downstream pressures $p_i^-$ for each inlet of the hepatic vein is provided. The upstream pressure $p^+$ at each of the portal vein tips (circles in FIG. 3) is assumed constant, and can be estimated by solving Darcy's law and optimizing over $p^+$ such that that the computed perfused flow through the hepatic vein inlets matches the three-dimensional CFD inlet flow profiles. Once $p^+$ is estimated, the blood flow inside the portal vein (304 in FIG. 3) is computed using the three-dimensional CFD solver. The effect of heat on the viscosity of the flow may be neglected. As a result, the flow related computation to simulate the blood flow in the liver can be performed prior to the simulation of heat diffusion.

In an advantageous implementation, the CFD computation can be performed using a full 3D Navier-Stokes viscous solver, expressed in a Eulerian framework which embeds the domain boundary using a level set representation of the segmented vessels. The porous flow can be calculated using a finite element method on the tetrahedral mesh of the liver anatomy. The resulting flow is tri-linearly rasterized on the Cartesian grid after computation. In an advantageous embodiment, the CFD and porous flow are calculated only once for a particular simulation, prior to simulating the heat diffusion and the cellular necrosis. In another embodiment, the CFD and porous flow are updated at every time step to take into account the changes in temperature.

Returning to FIG. 1, at step 110, heat diffusion in the liver due to ablation is simulated based on the simulated blood flow and the location of the virtual ablation probe. The diffusion of heat over time in the liver tissue is simulated by calculating the diffusion or progression of temperature change over time. A temperature distribution field is solved as a function of time using a partial differential equation or other equation. The numerical solution of the bio-heat transfer equations yields an underlying temperature distribution field that varies in space and time. Computing heat diffusion in biological tissue amounts to solving the coupled bio-heat equations derived from the theory of porous media, where each elementary volume is assumed to comprise a tissue fraction and a blood fraction. Two main simplifications for solving the coupled bio-heat equations are the Pennes model and the Wulff-Klinger (WK) model.

In the Pennes model, the blood temperature is assumed constant, which holds close to large vessels, where blood velocity is high. The Pennes model may be expressed as:

$$(1-\varepsilon)\rho_t c_t \frac{\partial T}{\partial t} = (1-\varepsilon)Q + (1-\varepsilon)\nabla \cdot (d_t \nabla T) + H(T_{b0} - T) \quad (1)$$

In the Wulff-Klinger model, equilibrium between tissue and blood temperatures is assumed ($T_t = T_b$), with a small blood volume fraction $\varepsilon$. This model is therefore well-suited small vessels, where blood velocity is low. The Wulff-Klinger model can be expressed as:

$$(1-\varepsilon)\rho_t c_t \frac{\partial T}{\partial t} = (1-\varepsilon)Q + (1-\varepsilon)\nabla \cdot (d_t \nabla T) + \varepsilon \rho_b c_b v \cdot \nabla T \quad (2)$$

In the above equations, T is the temperature, Q is the source term, v is the blood velocity, and $T_{bo}$ is the mean temperature of the blood in larger vessels (assumed constant). Subscripts t and b refer to tissue and blood phases respectively. Definitions and exemplary values of the remaining model parameters are provided in Table 1, below.

TABLE 1

Values of the parameters used in the simulation

| parameter | description | value |
|---|---|---|
| $\rho_b, \rho_t$ | blood and tissue densities | $1.06 \times 10^3$ kg m$^{-3}$ |
| $c_b$ | blood heat capacity | $4.18 \times 10^3$ J(kg K)$^{-1}$ |
| $c_t$ | tissue heat capacity | $3.6 \times 10^3$ J(kg K)$^{-1}$ |
| $c_t^*$ | tissue heat capacity in dead cells | $0.67 \times 10^3$ J(kg K)$^{-1}$ |
| $d_b, d_t$ | blood and tissue heat conductivities | $0.512 \times (1 + 0.00161 \times (T - 310))$ W/(m K)$^{-1}$ |
| H | convective transfer coefficient | $24.4 \times 10^4$ W (m$^3$ K)$^{-1}$ |
| ε | blood volume fraction | 0.1 |
| rt | permeability | $4.0 \times 10^{-2}$ m$^2$ |
| μ | dynamic viscosity of the blood | $4.6 \times (2.414 \times 10^{-5} \times 10^{247.8/(T-140)})$ Pw |
| $k_f$ | forward rate content | $3.33 \times 10^{-3}$ s$^{-1}$ |
| $k_b$ | backward rate content | $7.77 \times 10^{-3}$ s$^{-1}$ |
| $T_k$ | parameter of cell state model | 40.5° C. |

The main difference between the Pennes and the Wulff-Klinger models lies in their cooling terms (i.e., the last term of the right-hand side). The former acts as a volumetric homogeneous heat sink whilst the latter accounts for the directional effect of blood flow on the tissue temperature field. Therefore, both equations can be easily implemented in a modular way to cope with tissue inhomogeneity, by using one or the other cooling term.

Current imaging techniques may not allow estimation of an accurate ratio between blood and liver tissue. Large vessels are clearly identified in the patient-specific anatomical model of the liver, but small capillaries are difficult to image. Therefore embodiments of the present invention solve the bio-heat equation by combining the Pennes and Wulff-Klinger models in a unified and modular framework to model large and small vessels. Assuming that blood vessels and the surrounding tissue are isolated from each other, the liver temperature T is calculated by solving the diffusion equation $\rho_t c_t \partial T/\partial t = Q + \nabla \cdot (d_t \nabla T)$ everywhere in the domain. The cooling term $H(T_{b0}-T)/(1-\varepsilon)$ is added when a point belongs to a large vessel (Pennes model) and the cooling term $-\varepsilon \rho_b c_b v \cdot \nabla T/(1-\varepsilon)$ is added when a point belongs to a small vessel or the parenchyma (Wulff-Klinger model).

According to an advantageous embodiment, the bio-heat model is solved on an isotropic Cartesian grid using the Lattice Boltzmann method (LBM) with 7-connectivity topology (6 directions and a central position) and Neumann boundary conditions. Other grids with different connectivities can be used as well. The governing equations at a position $p=(x, y, z)$ or the edge $e_i$ can be expressed as:

$$f(p+e_i\Delta p, t+\Delta t) = f(p,t) + A[f^{eq}(p,t) - f(p,t)] + \omega \Delta t H(T(p,t) - T_{b0}) \quad (3)$$

where $c=\Delta_p/\Delta t$, $c_s^2 = 1/4$, $\Delta p$ is the spacing between points, and $f_i^{eq}(p,t) = \omega_i T(p,t)[1+e_i \cdot v/(cc_s^2)] \cdot f(p) = \{f_i(p)\}_{i=1 \ldots 7}$ is the vector of a distribution function with $f_i(p)$ the probability of finding a particle traveling along the edge e, of the node p at a given time, and $\omega = \{\omega_i\}_{i=1 \ldots 7}$ is the vector of weighting factors that depend on lattice connectivity. The temperature at each node can be calculated as: $T(p, t) = \Sigma_1^7 f_i(p,t)$, and is updated at every node of the grid for every time step t. It can be noted that the last term (reaction term) in equation (3) corresponds to the Pennes model. At points on the computational domain for which the Wulff-Klinger model is used, the reaction term to correspond to the Wulff-Klinger model. Using the level-set representation of the patient-specific anatomical model of the liver, the boundaries can be treated accurately without requiring advanced meshing techniques using linear interpolation. For a matter of stability, a Multiple-Relaxation-Time model is utilized, meaning that the vector of the distribution function is first projected onto the seven-dimensional space in which each component corresponds to a certain moment of the vector, then each component relaxes to the equilibrium with a different relaxation coefficient, and finally, the vector is projected back onto the original seven-dimension space. The collision matrix A can be expressed as $A=M^{-1}SM$, where:

$$M = \begin{pmatrix} 1 & 1 & 1 & 1 & 1 & 1 & 1 \\ 0 & 1 & -1 & 0 & 0 & 0 & 0 \\ 0 & 0 & 0 & 1 & -1 & 0 & 0 \\ 0 & 0 & 0 & 0 & 0 & 1 & -1 \\ 6 & -1 & -1 & -1 & -1 & -1 & -1 \\ 0 & 2 & 2 & -1 & -1 & -1 & -1 \\ 0 & 0 & 0 & 1 & 1 & -1 & -1 \end{pmatrix}$$

and $$S = \text{diag}(1, 1/\tau, 1/\tau, 1/\tau, 0.7519, 0.7519, 0.7519).$$

The relaxation time τ is directly related to the heat diffusion coefficient D through $\tau = 1/2 + 4D\Delta t/\Delta p^2$. The heat source term is modeled through a Dirichlet boundary condition at the location of the virtual probe. For example, in an exemplary implementation the heat source term is modeled through a Dirichlet boundary condition of 100° C. at the location of the virtual probe.

Returning to FIG. 1, at step 112, cellular necrosis in the liver is simulated based on the simulated heat diffusion. Heat from an ablation probe can cause cellular necrosis in the liver. In one embodiment, the tissue damage is modeled as using a three state model. The model computes the variation of concentration of live cells (A), vulnerable cells (C), and dead cells (D) over time according to the state equation: $A_{k_b}^{k_f} V^{k_f} \rightarrow D$ where $k_f$ and $k_b$ are the rates of cell damage and recovery, respectively. In particular, $k_f$ depends on the temperature through the equation: $k_f = k_f^- e^{T/T_k}(1-A)$ with $k_f^-$ being a scaling constant and $T_k$ a parameter that sets the rate of the exponential increase with temperature. This equation results in three simultaneous ordinary differential equations, that can be solved with a first order explicit scheme at each vertex of the Cartesian grid, yielding a spatially-varying cell state field that is then used in the LBM solver. In an exemplary implementation, the initial conditions can be chosen as A=0.99, V=0.01 and D=0.00. Exemplary values for the parameters $k_b$, $k_f^-$, and $T_k$ are shown in Table 1, above. Additionally, dead or damaged cells do not have the same heat capacity $c_t$ as live cells. This phenomenon can affect heat transfer and ablation extent. Accordingly, at each time step of the heat diffusion simulation, the state of the cell is updated at each point given the cell's current temperature, and the heat capacity of the cell is updated based on the state of the cell. The heat capacity $c_t$ is used if the cell is healthy or vulnerable, and the heat capacity $c_t^*$ is used for dead cells. Exemplary values for $c_t$ and $c_t^*$ are shown in Table 1.

Other cell death models may be used as well. For example, in another embodiment, the tissue damage can be modeled using a survival fraction index and an Arrhenius-like equation. The tissue damage model is experimentally determined, extracted from studies, or created from theory.

The survival fraction index indicates the amount of live versus dead cells in a region as a function of temperature. The survival fraction index is, calculated from the current temperature using an Arrhenius-like model. More precisely, the survival fraction index is the ratio of viable cells to the total number of cells in a region of interest. When the survival fraction index is <<1, cells in this spatial region are dead. The Arrhenius equation models the relationship of the survival fraction with respect to temperature.

Figure 4:
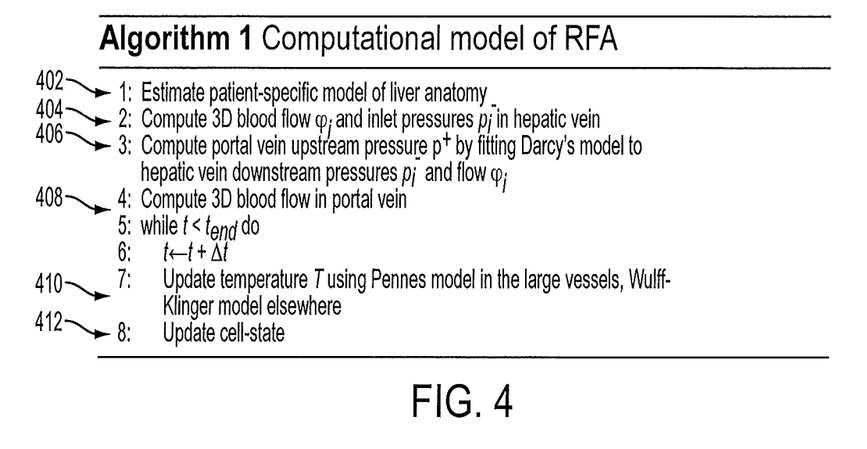
FIG. 4 illustrates an algorithm for implementing a computational model for simulating radio frequency ablation (ABA), according to an embodiment of the present invention.

FIG. 4 illustrates an algorithm for implementing a computational model for simulating radio frequency ablation (RFA), according to an embodiment of the present invention. The algorithm of FIG. 4 can be used to implement steps 106-112 of FIG. 1. As illustrated in FIG. 4, at 402, the patient-specific model of liver anatomy is estimated. At 404, compute 3D blood flow $\varphi$ and inlet pressures $p_i^-$ in the hepatic vein are computed using the CFD solver. At 406, portal vein upstream pressure $p^+$ is computed by fitting Darcy's model to the hepatic vein downstream pressures $p_i^-$ and flow $\varphi_i$. At 408, 3D blood flow in portal vein is computed using the CFD solver. The blood flow and pressures in the hepatic vein and the portal vein provide Dirichlet boundary conditions for computing the blood velocity inside the parenchyma using the finite element method. Once the blood flow is simulated in the whole patient-specific model of the liver, operations 410 and 412 are performed at each time step (t) between while $t<t_{end}$. At 410, the temperature T using Pennes model in the large vessels and Wulff-Klinger model elsewhere (e.g., parenchyma). In particular, the collisions for each node of the level set representation are calculated by calculating distribution function $f_i(x)$ for edge (e.g., i=1 . . . 7) for each node based on the collision matrix A, which depends on the heat diffusion equation at each node. At nodes associated with large vessels, the Pennes model is used for the heat diffusion equation, and at the remaining nodes (e.g., nodes associated with the parenchyma), the Wulff-Klinger model is used for the heat-diffusion equation. The collisions calculated for each node are used to calculate the temperature at each node as $T(p, t)=\Sigma_1^7 f_i(p,t)$. At 412, the cell-state is updated at each node of the level set representation using the cellular necrosis model based on the simulated temperature for each node. Although it is possible to process the nodes sequentially, according to an advantageous implementation, the computation of the temperature using the above described LBM implementation and the computation of the cellular necrosis at each node can be performed in parallel, for example using a massively parallel architecture, such as a GPU.

Returning to FIG. 1, at step 114 temperature maps and a visualization of a simulated necrosis area are output. For example, the temperature maps and simulated necrosis area visualization can be output by displaying the temperature maps and simulated necrosis area visualization on a display of a computer system using color coding, streamlines or iso-contours. The map can be updated at every time step or every N time steps to show the dynamics of the system.

At step 116, a user input is interactively received to change the location of the virtual ablation probe or to change model parameters. Using the parallel LBM implementation for solving the heat diffusion equations and the cellular necrosis model provides an efficient liver ablation simulation that can be performed in near real-time in a clinical setting. This allows a user (e.g., a physician) to interactively change the ablation probe position to get liver ablation simulations for ablation at different positions within the liver. This also allows a user to interactively modify model parameters, such as parameters used in the heat diffusion model, the cellular necrosis model, or the computation model used for the blood flow simulation. Once the user input is received, the method returns to step 108 and re-computes the blood-flow simulation, the heat diffusion in the liver, and the cellular necrosis with the modified ablation probe position and/or the modified model parameters, and display the updated maps. According to a possible implementation, if only model parameters used in the blood flow simulation are not modified in step 116, the method can instead return to step 110 and repeat steps 110-114 without first re-simulating the blood flow in the liver. For example, if the user input only changes the position of the virtual ablation probe, the method can return to step 110 simulate the heat diffusion and cellular necrosis based on the modified ablation probe position using the previously calculated blood flow simulation results.

Figure 5:
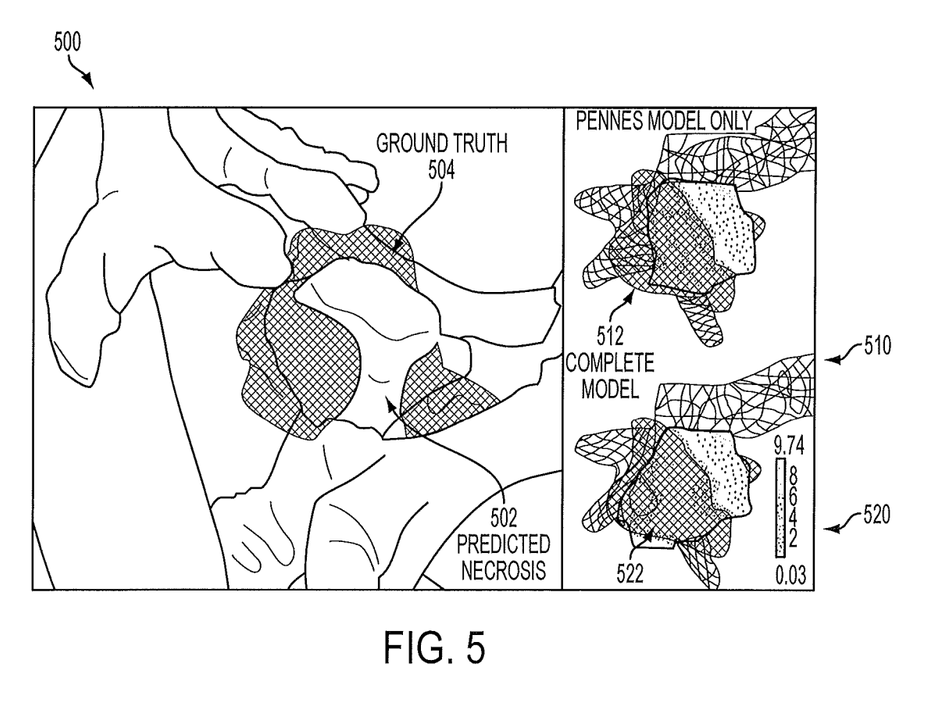
FIG. 5 illustrates an exemplary visualization of a simulated necrosis area.

The proposed framework has been evaluated on a patient for whom a tumor was ablated as follows. The ablation probe was serially deployed within the tumor to 3 cm. The target temperature reaches 105° C. (based on probe thermisters) and was maintained for seven minutes. The patient-specific anatomical model for the patient was extracted from a standard preoperative CT image. The RFA protocol was simulated by placing the virtual probe at the center of the tumor. Cells within a 3 cm diameter sphere around the probe were heated at 105° C. for time period of seven minutes. The simulation continued for three additional minutes to reach a steady state. Two experiments were carried on: 1) Pennes model only (no advection in the parenchyma); and 2) complete model. These two simulations showed the cooling effect of the big veins sue to the reaction term on the necrosis area, as well as the heat advection of the small arteries, which appear to influence the extent of ablated tissue. FIG. 5 illustrates an exemplary visualization of a simulated necrosis area. As shown in FIG. 5, image 500 shows the predicted necrosis area 502 computed in the simulation with the complete model overlaid with the ground truth cellular necrosis area 504. As can be seen in image 500, the predicted necrotic extent from the simulated necrosis area 502 qualitatively agrees with the ground truth cellular necrosis 504 from a post-operative MRI of the patient. Images 510 and 520 show point-to-mesh error maps between the predicted necrosis area and ground truth necrosis area for the Pennes only simulation and the complete model simulation, respectively. It can be seen in images 510 and 520 that the modeling of the heat advection in the parenchyma provides a more accurate prediction of the necrosis area, particularly at the location 512 and 522. The average point-to-mesh error for the Pennes model only simulation is 2.7±1.9 mm and the average point-to-mesh error for the complete model is 2.6±1.8 mm. The simulation using the complete model predicted an entire covering of the lesion, as it has been observed, which is an important aspect to capture for optimal planning.

The present inventors evaluated the computational model for simulating radiofrequency ablation in the liver by comparing its behavior on a regular cuboid domain with the 3D analytical solution of an instantaneous point source of mass M released at location $x_0=(x_0, y_0, z_0)$ and time $t_0$ with $v=(u,v,w)$, of the advection-diffusion equation $\partial T/\partial t + v \cdot \nabla T = \nabla(d\nabla T)$:

$$T(x, t) = \frac{M}{[4\pi(t-t_0)D]^{3/2}} \exp\left[-\frac{\|x-x_0-(t-t_0)v\|^2}{4D(t-t_0)}\right].$$

Figure 6:
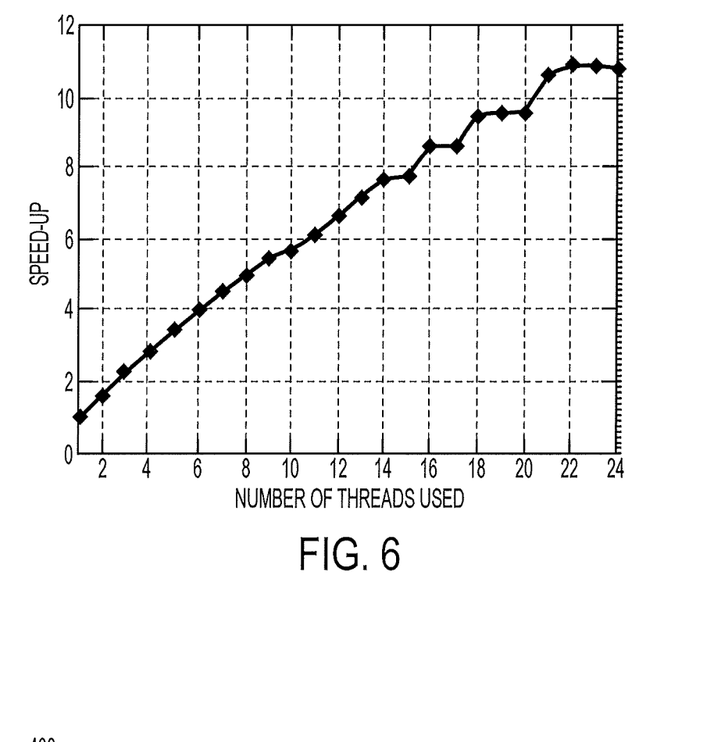
FIG. 6 illustrates an example of the speed-up achieved using multi-threading with the proposed LBM solver.
Figure 7:
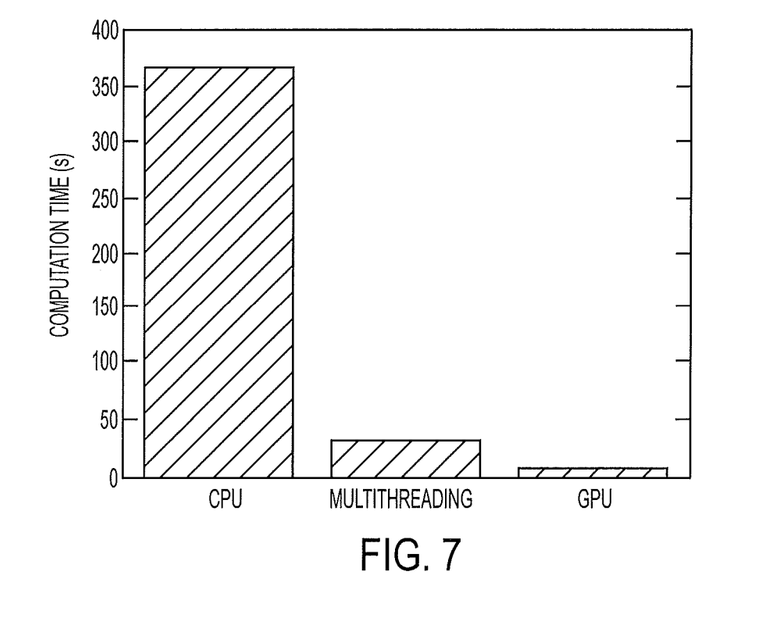
FIG. 7 illustrates a comparison of computational time for CPU, multithreading, and GPU implementations.

Parameters were selected to get the heat diffusion in the physiological range: $D=0.1$ mm$^2$/s, $v=(2, 0, 0)$mm/s, and take $M=35000°$ C./mm$^3$, $t_0=-50$ s, yielding a Gaussian-shape source term of 70° C. at the center of the beam at time $t=0$ s, thus minimizing the effects of the boundary conditions. In the LBM solver, the temperature values were initialized at each point with the analytical solution at time $t=0$ s, and the temperature was observed at several points of the domain. The framework described herein was qualitatively close to the analytical solution. For a given resolution (e.g., 0.5 mm, 1 mm, 2 mm, 5 mm, etc.), an upper and lower bound for the time-step were provided by the simulated physics and Courant-Friedrichs-Lewy conditions. As expected, the more accurate smaller the spatial resolution, the more accurate the simulated solution is compared to the analytical solution. A time step of 75 ms and a resolution of 1 mm provides a good compromise between accuracy and computational cost. The present inventors conducted the experiments on a Windows 7 desktop machine (Intel Xeon, 2.80 Hz, 45 GB RAM) with a NVidia Quadro 6000 1.7 GB. The present inventors compared the simulations being performed by a single-core implementation with a CPU, parallel optimization (Open MP), and implementation in graphical processing units (GPU) on CUDA. FIG. 6 illustrates an example of the speed-up achieved using multi-threading. As shown in FIG. 6, as the number of parallel threads increase, speed-up of 11 times the speed of the a single thread can be achieved. FIG. 7 illustrates a comparison of computational time for CPU, multithreading, and GPU implementations. As shown in FIG. 7, multithreading using parallel optimization with OpenMP is 11 times faster than single core implementation on a CPU, and GPE implementation on CUDA is 45 times faster than single core implementation of a CPU. The GPU implementation achieved a speed-up of 60 times faster than finite element method (FEM) with similar accuracy.

Figure 8:
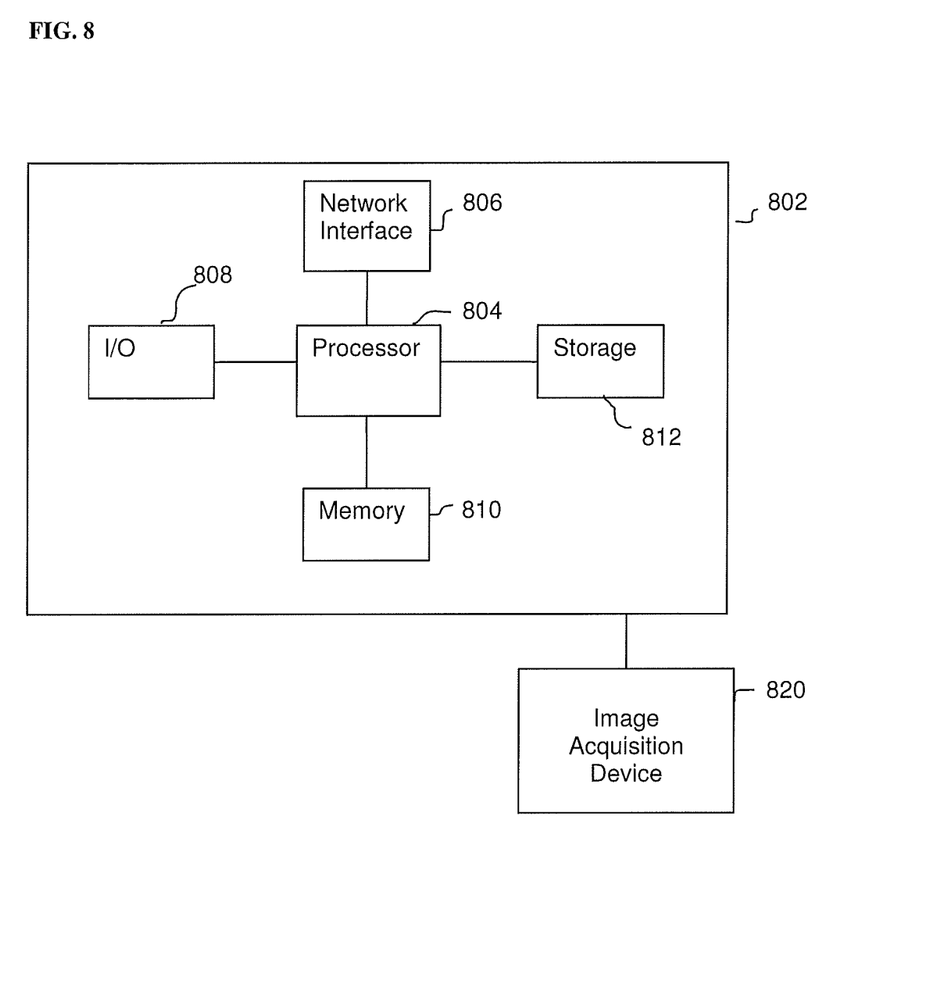
FIG. 8 is a high-level block diagram of a computer capable of implementing the present invention.

The above-described methods for patient-specific simulation of liver tumor ablation can be implemented on a computer using well-known computer processors, memory units, storage devices, computer software, and other components. A high-level block diagram of such a computer is illustrated in FIG. 8. Computer 802 contains a processor 804, which controls the overall operation of the computer 802 by executing computer program instructions which define such operation. The computer program instructions may be stored in a storage device 812 (e.g., magnetic disk) and loaded into memory 810 when execution of the computer program instructions is desired. Thus, the steps of the methods of FIGS. 1 and 4 may be defined by the computer program instructions stored in the memory 810 and/or storage 812 and controlled by the processor 804 executing the computer program instructions. An image acquisition device 820, such as a CT scanning device, C-arm image acquisition device, MR scanning device, Ultrasound device, etc., can be connected to the computer 802 to input image data to the computer 802. It is possible to implement the image acquisition device 820 and the computer 802 as one device. It is also possible that the image acquisition device 820 and the computer 802 communicate wirelessly through a network. The computer 802 also includes one or more network interfaces 806 for communicating with other devices via a network. The computer 802 also includes other input/output devices 808 that enable user interaction with the computer 802 (e.g., display, keyboard, mouse, speakers, buttons, etc.). Such input/output devices 808 may be used in conjunction with a set of computer programs as an annotation tool to annotate volumes received from the image acquisition device 820. One skilled in the art will recognize that an implementation of an actual computer could contain other components as well, and that FIG. 8 is a high level representation of some of the components of such a computer for illustrative purposes.

The foregoing Detailed Description is to be understood as being in every respect illustrative and exemplary, but not restrictive, and the scope of the invention disclosed herein is not to be determined from the Detailed Description, but rather from the claims as interpreted according to the full breadth permitted by the patent laws. It is to be understood that the embodiments shown and described herein are only illustrative of the principles of the present invention and that various modifications may be implemented by those skilled in the art without departing from the scope and spirit of the invention. Those skilled in the art could implement various other feature combinations without departing from the scope and spirit of the invention.

The invention claimed is:

1. A method for interactive patient-specific simulation of liver tumor ablation, comprising:
    estimating, from medical image data of a patient, a patient-specific anatomical model of a liver of the patient and a circulatory system of the liver;
    generating a computational domain from the patient-specific anatomical model of the liver;
    simulating blood flow in the liver and the circulatory system of the liver based on the patient-specific anatomical model;
    simulating heat diffusion due to ablation based on a virtual ablation probe position corresponding to a possible ablation probe position for an ablation procedure for the patient and the simulated blood flow in the liver and the circulatory system of the liver by solving a bio-heat equation at each of a plurality of nodes of the computational domain; and
    computing cellular necrosis in the liver based on the simulated heat diffusion and updating tissue parameters based on a computed cellular state to provide a predicted necrotic extent resulting from the ablation procedure for the patient with the possible ablation probe position.

2. The method of claim 1, further comprising:
    generating a visualization of a temperature map of the liver based on the simulated heat diffusion; and
    generating a visualization of a computed necrosis region.

3. The method of claim 2, further comprising:
    receiving, interactively, a user input indicating a modified position of the ablation probe;
    re-simulating the heat diffusion and the cellular necrosis based on the modified position of the virtual ablation probe; and
    re-generating the visualization of the temperature map and the visualization of the computed necrosis region.

4. The method of claim 2, further comprising:
    receiving, interactively, a user input to modify at least one parameter of at least one of the patient-specific anatomical model, a computational fluid dynamics model used to simulate the blood flow, the bio-heat equation, or a cellular necrosis model used to simulate the cellular necrosis;
    re-simulating the blood flow, heat diffusion, and cellular necrosis with the modified at least one parameter; and
    generating the visualization of the temperature map and the visualization of the computed necrosis region.

5. The method of claim 1, wherein estimating, from medical image data of a patient, a patient-specific anatomical model of a liver of the patient and a venous system of the liver comprises:

estimating a patient-specific anatomical model of the liver including a liver parenchyma, at least one tumor, a hepatic vein, a vena cava, a portal vein, and a hepatic artery.

6. The method of claim 1, wherein simulating blood flow in the liver and the circulatory system of the liver based on the patient-specific anatomical model comprises:

calculating 3D blood flow and inlet pressures in a hepatic vein over a plurality of time steps using computational fluid dynamics (CFD) simulation;

calculating portal vein and hepatic artery upstream pressures over the plurality of time steps based on the blood flow and the inlet pressures in the hepatic vein; and calculating 3D blood flow in the portal vein and hepatic artery over the plurality of time steps based on the portal vein upstream pressures using CFD simulation.

7. The method of claim 1, wherein simulating blood flow in the liver and the circulatory system of the liver based on the patient-specific anatomical model comprises:

simulating blood flow in the circulatory system of the liver at each of a plurality of time steps using a computational fluid dynamics (CFD) solver on a level set representation of the circulatory system of the liver; and simulating blood flow in the liver parenchyma by calculating porous blood flow using a porous blood flow solver.

8. The method of claim 7, wherein simulating blood flow in a liver parenchyma by calculating porous blood flow using a porous blood flow solver comprises:

simulating blood flow in the liver parenchyma by calculating porous blood flow on a tetrahedral mesh of the liver using a finite element method (FEM).

9. The method of claim 1, wherein simulating heat diffusion due to ablation based on a virtual ablation probe position corresponding to a possible ablation probe position for an ablation procedure for the patient and the simulated blood flow in the liver and the circulatory system of the liver by solving a bio-heat equation at each of a plurality of nodes of the computational domain comprises:

solving a bio-heat equation at each of the plurality of nodes of a level-set representation of the patient-specific anatomical model using a Lattice-Boltzmann method (LBM).

10. The method of claim 9, wherein solving a bio-heat equation at each of the plurality of nodes of a level-set representation of the patient-specific anatomical model using a Lattice-Boltzmann method (LBM) comprises:

for each of the plurality of nodes:
calculating a temperature at each of a plurality of time steps by solving a first bio-heat equation having a first cooling term if the node belongs to a hepatic vein, a hepatic artery, or a portal vein, and a second bio-heat equation having a second cooling term if the node belongs to a liver parenchyma.

11. The method of claim 10, wherein the first bio-heat equation is a Pennes model bio-heat equation and the second bio-heat equation is a Wulff-Klinger model bio-heat equation.

12. The method of claim 1, wherein simulating cellular necrosis in the liver based on the simulated heat diffusion comprises:

calculating a cell state for each of the plurality of nodes of the computational domain at each of a plurality of time steps based on a respective calculated temperature at each of the plurality of nodes at each of the plurality of time steps; and updating a heat capacity at each of a plurality of nodes at each of the plurality of time steps based on the calculated cell state.

13. The method of claim 1, wherein generating a computational domain of the patient-specific anatomical model of the liver comprises:

discretizing a domain of the patient-specific model of the liver using a Cartesian lattice and a level-set representation in which each node is connected via edges to a predetermined number of neighboring nodes.

14. The method of claim 13, wherein simulating heat diffusion due to ablation based on a virtual ablation probe position corresponding to a possible ablation probe position for an ablation procedure for the patient and the simulated blood flow in the liver and the circulatory system of the liver by solving a bio-heat equation at each of a plurality of nodes of the computational domain comprises:

for each node of the level-set representation of the patient-specific anatomical model of the liver on a Cartesian grid:

calculating, at each of a plurality of time steps, collisions of particles for each edge connected to the node based on a distribution function calculated for each edge, wherein each distribution function is based on a collision matrix that is dependent on a first bio-heat equation if the node is associated with a large vein in the liver and dependent on a second bio-heat equation if the node is associated with a liver parenchyma; and calculating, at each of the plurality of time steps, a temperature at the node as a sum of the collisions of particles calculated for all of the edges connected to the node.

15. The method of claim 1, wherein the heat diffusion is simulated at each of a plurality of time steps, and computing cellular necrosis in the liver based on the simulated heat diffusion comprises:

calculating a variation of a concentration of alive cells, vulnerable cells, and dead cells in the liver over a plurality of time steps based on the simulated heat diffusion.

16. The method of claim 9, wherein solving a bio-heat equation at each of the plurality of nodes of a level-set representation of the patient-specific anatomical model using a Lattice-Boltzmann method (LBM) comprises:

at each of a plurality of time steps, solving a bio-heat equation for multiple ones of the plurality of nodes of the level-set representation in parallel.

17. The method of claim 16, wherein computing cellular necrosis in the liver based on the simulated heat diffusion comprises:

at each of the plurality of time steps, simulating cellular necrosis for the multiple ones of the plurality of nodes in parallel based on a simulated temperature calculated at each node.

18. The method of claim 1, wherein the virtual ablation probe position is a user-defined ablation probe position.

19. The method of claim 1, further comprising:

automatically selecting a plurality of possible ablation probe positions for the ablation procedure for the patient;

simulating the heat diffusion and computing the cellular necrosis for each of the plurality of possible ablation probe positions;
determining one or more optimal ablation probe positions for the ablation procedure for the patient based on the simulated heat diffusion and computed cellular necrosis for each of the plurality of possible ablation probe positions; and
generating a display of the one or more optimal ablation probe positions for the ablation procedure for the patient determined based on the plurality of possible ablation probe positions.

20. An apparatus for interactive patient-specific simulation of liver tumor ablation, comprising:
a processor; and
a memory storing computer program instructions, which when executed by the processor cause the processor to perform operations comprising:
estimating, from medical image data of a patient, a patient-specific anatomical model of a liver of the patient and a circulatory system of the liver;
generating a computational domain from the patient-specific anatomical model of the liver;
simulating blood flow in the liver and the circulatory system of the liver based on the patient-specific anatomical model;
simulating heat diffusion due to ablation based on a virtual ablation probe position corresponding to a possible ablation probe position for an ablation procedure for the patient and the simulated blood flow in the liver and the circulatory system of the liver by solving a bio-heat equation at each of a plurality of nodes of the computational domain; and
computing cellular necrosis in the liver based on the simulated heat diffusion and updating tissue parameters based on a computed cellular state to provide a predicted necrotic extent resulting from the ablation procedure for the patient with the possible ablation probe position.

21. The apparatus of claim 20, wherein the operations further comprise:
generating a visualization of a temperature map of the liver based on the simulated heat diffusion; and
generating a visualization of a computed necrosis region.

22. The apparatus of claim 21, wherein the operations further comprise:
receiving, interactively, a user input indicating a modified position of the ablation probe;
re-simulating the heat diffusion and the cellular necrosis based on the modified position of the virtual ablation probe; and
re-generating the visualization of the temperature map and the visualization of the computed necrosis region.

23. The apparatus of claim 21, wherein the operations further comprise:
receiving, interactively, a user input to modify at least one parameter of at least one of the patient-specific anatomical model, a computational fluid dynamics model used to simulate the blood flow, the bio-heat equation, or a cellular necrosis model used to simulate the cellular necrosis;
re-simulating the blood flow, heat diffusion, and cellular necrosis with the modified at least one parameter; and
re-generating the visualization of the temperature map and the visualization of the computed necrosis region.

24. The apparatus of claim 20, wherein estimating, from medical image data of a patient, a patient-specific anatomical model of a liver of the patient and a venous system of the liver comprises:
estimating a patient-specific anatomical model of the liver including a liver parenchyma, at least one tumor, a hepatic vein, a vena cava, a portal vein, and a hepatic artery.

25. The apparatus of claim 20, wherein simulating blood flow in the liver and the circulatory system of the liver based on the patient-specific anatomical model comprises:
calculating 3D blood flow and inlet pressures in a hepatic vein over a plurality of time steps using computational fluid dynamics (CFD) simulation;
calculating portal vein and hepatic artery upstream pressures over the plurality of time steps based on the blood flow and the inlet pressures in the hepatic vein; and
calculating 3D blood flow in the portal vein and hepatic artery over the plurality of time steps based on the portal vein upstream pressures using CFD simulation.

26. The apparatus of claim 20, wherein simulating blood flow in the liver and the circulatory system of the liver based on the patient-specific anatomical model comprises:
simulating blood flow in the circulatory system of the liver at each of a plurality of time steps using a computational fluid dynamics (CFD) solver on a level set representation of the circulatory system of the liver; and
simulating blood flow in a liver parenchyma by calculating porous blood flow using a porous blood flow solver.

27. The apparatus of claim 26, wherein simulating blood flow in a liver parenchyma by calculating porous blood flow using a porous blood flow solver comprises:
simulating blood flow in the liver parenchyma by calculating porous blood flow on a tetrahedral mesh of the liver using a finite element method (FEM).

28. The apparatus of claim 20, wherein simulating heat diffusion due to ablation based on a virtual ablation probe position corresponding to a possible ablation probe position for an ablation procedure for the patient and the simulated blood flow in the liver and the circulatory system of the liver by solving a bio-heat equation at each of a plurality of nodes of the computational domain comprises:
solving a bio-heat equation at each of the plurality of nodes of a level-set representation of the patient-specific anatomical model using a Lattice-Boltzmann method (LBM).

29. The apparatus of claim 28, wherein solving a bio-heat equation at each of the plurality of nodes of a level-set representation of the patient-specific anatomical model using a Lattice-Boltzmann method (LBM) comprises:
calculating, for each of the plurality of nodes, a temperature at each of a plurality of time steps by solving a first bio-heat equation having a first cooling term if the node belongs to a hepatic vein, a hepatic artery, or a portal vein, and a second bio-heat equation having a second cooling term if the node belongs to a liver parenchyma.

30. The apparatus of claim 29, wherein the first bio-heat equation is a Pennes model bio-heat equation and the second bio-heat equation is a Wulff-Klinger model bio-heat equation.

31. The apparatus of claim 20, wherein simulating cellular necrosis in the liver based on the simulated heat diffusion comprises:
calculating a cell state for each of the plurality of nodes of the computational domain at each of the plurality of time steps based on a respective calculated temperature at each of a plurality of nodes at each of the plurality of time steps; and updating a heat capacity at each of a plurality of nodes at each of the plurality of time steps based on the calculated cell state.

32. The apparatus of claim 20, wherein generating a computational domain of the patient-specific anatomical model of the liver comprises:

discretizing a domain of the patient-specific model of the liver using a Cartesian lattice and a level-set representation in which each node is connected via edges to a predetermined number of neighboring nodes.

33. The apparatus of claim 32, wherein simulating heat diffusion due to ablation based on a virtual ablation probe position corresponding to a possible ablation probe position for an ablation procedure for the patient and the simulated blood flow in the liver and the circulatory system of the liver by solving a bio-heat equation at each of a plurality of nodes of the computational domain comprises:

calculating, at each of a plurality of time steps for each node of the level-set representation of the patient-specific anatomical model of the liver on a Cartesian grid, collisions of particles for each edge connected to the node based on a distribution function calculated for each edge, wherein each distribution function is based on a collision matrix that is dependent on a first bio-heat equation if the node is associated with a large vein in the liver and dependent on a second bio-heat equation if the node is associated with a liver parenchyma; and calculating, at each of the plurality of time steps, a temperature at the node a sum of the collisions of particles calculated for all of the edges connected to the node.

34. The apparatus of claim 20, wherein the heat diffusion is simulated at each of a plurality of time steps, and computing cellular necrosis in the liver based on the simulated heat diffusion comprises:

calculating a variation of a concentration of alive cells, vulnerable cells, and dead cells in the liver over a plurality of time steps based on the simulated heat diffusion.

35. The apparatus of claim 28, wherein solving a bio-heat equation at each of the plurality of nodes of a level-set representation of the patient-specific anatomical model using a Lattice-Boltzmann method (LBM) comprises:

solving, at each of a plurality of time steps, a bio-heat equation for multiple ones of the plurality of nodes of the level-set representation in parallel.

36. The apparatus of claim 35, wherein computing cellular necrosis in the liver based on the simulated heat diffusion comprises:

at each of the plurality of time steps, simulating cellular necrosis for the multiple ones of the plurality of nodes in parallel based on a simulated temperature calculated at each node.

37. The apparatus of claim 20, wherein the virtual ablation probe position is a user-defined ablation probe position.

38. The apparatus of claim 20, wherein the operations further comprise:

automatically selecting a plurality of possible ablation probe positions for the ablation procedure for the patient;

simulating the heat diffusion and computing the cellular necrosis for each of the plurality of possible ablation probe positions;

determining one or more optimal ablation probe positions for the ablation procedure for the patient based on the simulated heat diffusion and computed cellular necrosis for each of the plurality of possible ablation probe positions; and generating a display of the one or more optimal ablation probe positions for the ablation procedure for the patient determined based on the plurality of possible ablation probe positions.

39. A non-transitory computer readable medium storing computer program instructions for interactive patient-specific simulation of liver tumor ablation, the computer program instructions when executed on a processor cause the processor to perform operations comprising:

estimating, from medical image data of a patient, a patient-specific anatomical model of a liver of the patient and a circulatory system of the liver;

generating a computational domain from the patient-specific anatomical model of the liver;

simulating blood flow in the liver and the circulatory system of the liver based on the patient-specific anatomical model;

simulating heat diffusion due to ablation based on a virtual ablation probe position corresponding to a possible ablation probe position for an ablation procedure for the patient and the simulated blood flow in the liver and the circulatory system of the liver by solving a bio-heat equation at each of a plurality of nodes of the computational domain; and computing cellular necrosis in the liver based on the simulated heat diffusion and updating tissue parameters based on a computed cellular state to provide a predicted necrotic extent resulting from the ablation procedure for the patient with the possible ablation probe position.

40. The non-transitory computer readable medium of claim 39, wherein the operations further comprise:

generating a visualization of a temperature map of the liver based on the simulated heat diffusion; and generating a visualization of a computed necrosis region.

41. The non-transitory computer readable medium of claim 40, wherein the operations further comprise:

receiving, interactively, a user input indicating a modified position of the ablation probe;

re-simulating the heat diffusion and the cellular necrosis based on the modified position of the virtual ablation probe; and re-generating the visualization of the temperature map and the visualization of the computed necrosis region.

42. The non-transitory computer readable medium of claim 40, wherein the operations further comprise:

receiving, interactively, a user input to modify at least one parameter of at least one of the patient-specific anatomical model, a computational fluid dynamics model used to simulate the blood flow, the bio-heat equation, or a cellular necrosis model used to simulate the cellular necrosis;

re-simulating the blood flow, heat diffusion, and cellular necrosis with the modified at least one parameter; and generating the visualization of the temperature map and the visualization of the computed necrosis region.

43. The non-transitory computer readable medium of claim 39, wherein estimating, from medical image data of a patient, a patient-specific anatomical model of a liver of the patient and a venous system of the liver comprises:

estimating a patient-specific anatomical model of the liver including a liver parenchyma, at least one tumor, a hepatic vein, a vena cava, a portal vein, and a hepatic artery.

44. The non-transitory computer readable medium of claim 39, wherein simulating blood flow in the liver and the circulatory system of the liver based on the patient-specific anatomical model comprises:
calculating 3D blood flow and inlet pressures in a hepatic vein over a plurality of time steps using computational fluid dynamics (CFD) simulation;
calculating portal vein and hepatic artery upstream pressures over the plurality of time steps based on the blood flow and the inlet pressures in the hepatic vein; and
calculating 3D blood flow in the portal vein and hepatic artery over the plurality of time steps based on the portal vein upstream pressures using CFD simulation.

45. The non-transitory computer readable medium of claim 39, wherein simulating blood flow in the liver and the circulatory system of the liver based on the patient-specific anatomical model comprises:
simulating blood flow in the circulatory system of the liver at each of a plurality of time steps using a computational fluid dynamics (CFD) solver on a level set representation of the circulatory system of the liver; and
simulating blood flow in a liver parenchyma by calculating porous blood flow using a porous blood flow solver.

46. The non-transitory computer readable medium of claim 45, wherein simulating blood flow in the liver parenchyma by calculating porous blood flow using a porous blood flow solver comprises:
simulating blood flow in the liver parenchyma by calculating porous blood flow on a tetrahedral mesh of the liver using a finite element method (FEM).

47. The non-transitory computer readable medium of claim 39, wherein simulating heat diffusion due to ablation based on a virtual ablation probe position corresponding to a possible ablation probe position for an ablation procedure for the patient and the simulated blood flow in the liver and the circulatory system of the liver by solving a bio-heat equation at each of a plurality of nodes of the computational domain comprises:
solving a bio-heat equation at each of the plurality of nodes of a level-set representation of the patient-specific anatomical model using a Lattice-Boltzmann method (LBM).

48. The non-transitory computer readable medium of claim 47, wherein solving a bio-heat equation at each of the plurality of nodes of a level-set representation of the patient-specific anatomical model using a Lattice-Boltzmann method (LBM) comprises:
for each of the plurality of nodes:
calculating a temperature at each of a plurality of time steps by solving a first bio-heat equation having a first cooling term if the node belongs to a hepatic vein, a hepatic artery, or a portal vein, and a second bio-heat equation having a second cooling term if the node belongs to a liver parenchyma.

49. The non-transitory computer readable medium of claim 48, wherein the first bio-heat equation is a Pennes model bio-heat equation and the second bio-heat equation is a Wulff-Klinger model bio-heat equation.

50. The non-transitory computer readable medium of claim 39, wherein simulating cellular necrosis in the liver based on the simulated heat diffusion comprises:

calculating a cell state for each of the plurality of nodes of the computational domain at each of a plurality of time steps based on a respective calculated temperature at each of the plurality of nodes at each of the plurality of time steps; and
updating a heat capacity at each of a plurality of nodes at each of the plurality of time steps based on the calculated cell state.

51. The non-transitory computer readable medium of claim 39, wherein generating a computational domain of the patient-specific anatomical model of the liver comprises:
discretizing a domain of the patient-specific model of the liver using a Cartesian lattice and a level-set representation in which each node is connected via edges to a predetermined number of neighboring nodes.

52. The non-transitory computer readable medium of claim 51, wherein simulating heat diffusion due to ablation based on a virtual ablation probe position corresponding to a possible ablation probe position for an ablation procedure for the patient and the simulated blood flow in the liver and the circulatory system of the liver by solving a bio-heat equation at each of a plurality of nodes of the computational domain comprises:
for each node of the level-set representation of the patient-specific anatomical model of the liver on a Cartesian grid:
calculating, at each of a plurality of time steps, collisions of particles for each edge connected to the node based on a distribution function calculated for each edge, wherein each distribution function is based on a collision matrix that is dependent on a first bio-heat equation if the node is associated with a large vein in the liver and dependent on a second bio-heat equation if the node is associated with a liver parenchyma; and
calculating, at each of the plurality of time steps, a temperature at the node as a sum of the collisions of particles calculated for all of the edges connected to the node.

53. The non-transitory computer readable medium of claim 39, wherein the heat diffusion is simulated at each of a plurality of time steps, and computing cellular necrosis in the liver based on the simulated heat diffusion comprises:
calculating a variation of a concentration of alive cells, vulnerable cells, and dead cells in the liver over a plurality of time steps based on the simulated heat diffusion.

54. The non-transitory computer readable medium of claim 47, wherein solving a bio-heat equation at each of the plurality of nodes of a level-set representation of the patient-specific anatomical model using a Lattice-Boltzmann method (LBM) comprises:
at each of a plurality of time steps, solving a bio-heat equation for multiple ones of the plurality of nodes of the level-set representation in parallel.

55. The non-transitory computer readable medium of claim 54, wherein computing cellular necrosis in the liver based on the simulated heat diffusion comprises:
at each of the plurality of time steps, simulating cellular necrosis for the multiple ones of the plurality of nodes in parallel based on a simulated temperature calculated at each node.

56. The non-transitory computer readable medium of claim 39, wherein the virtual ablation probe position is a user-defined ablation probe position.

57. The non-transitory computer readable medium of claim 39, wherein the operations further comprise:

automatically selecting a plurality of possible ablation probe positions for the ablation procedure for the patient;
simulating the heat diffusion and computing the cellular necrosis for each of the plurality of possible ablation probe positions;
determining one or more optimal ablation probe positions for the ablation procedure for the patient based on the simulated heat diffusion and computed cellular necrosis for each of the plurality of possible ablation probe positions; and
generating a display of the one or more optimal ablation probe positions for the ablation procedure for the patient determined based on the plurality of possible ablation probe positions.

* * * * *